(12) United States Patent
Yock et al.

(10) Patent No.: US 6,346,098 B1
(45) Date of Patent: Feb. 12, 2002

(54) METHODS AND KITS FOR LOCALLY ADMINISTERING AN ACTIVE AGENT TO AN INTERSTITIAL SPACE OF A HOST

(75) Inventors: Paul G. Yock; Ali H. Hassan; Alan Ching Yeun Yeung; Andrew Carter; Mehrdad Rezaee; Niall Herity; Sidney Lo; Peter J. Fitzgerald, all of Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/519,950

(22) Filed: Mar. 7, 2000

(51) Int. Cl.[7] .................. A61M 25/00; A61K 38/00; A61K 48/00; A61K 31/715

(52) U.S. Cl. ............... 604/508; 604/507; 514/2; 514/44; 514/54

(58) Field of Search ............... 514/2, 44, 54; 604/96.01, 508, 509, 510, 507; 607/1; 11/11

(56) References Cited

U.S. PATENT DOCUMENTS

| | | | |
|---|---|---|---|
| 4,459,977 A | 7/1984 | Pizon et al. | 600/17 |
| 4,689,041 A | 8/1987 | Corday et al. | 604/509 |
| 4,934,996 A | 6/1990 | Mohl et al. | 600/17 |
| 5,011,468 A | 4/1991 | Lundquist et al. | 600/18 |
| 5,533,957 A | 7/1996 | Aldea | 600/16 |
| 5,597,377 A | 1/1997 | Aldea | 600/16 |
| 5,824,071 A | 10/1998 | Nelson et al. | 606/194 |
| 5,874,402 A * | 2/1999 | Singh et al. | 514/2 |
| 5,885,238 A | 3/1999 | Stevens et al. | 604/6.14 |
| 5,913,842 A | 6/1999 | Boyd et al. | 604/28 |
| 5,922,687 A | 7/1999 | Mann et al. | 514/44 |
| 5,925,683 A | 7/1999 | Park | 514/772.1 |
| 5,985,847 A | 11/1999 | Carson et al. | 514/44 |

OTHER PUBLICATIONS

Baumbach et al. (1999). "Local drug delivery: Impact of pressure, substance characteristics, and stenting on drug transfer into the arterial wall" *Catheterization and Cardiovascular Interventions*, vol. 47: 102–106.

Boekstegers et al. (1999). "Regional and highly efficient myocardial gene transfer by selective pressure–regulated retroinfusion of coronary veins" *JACC*, Abstracts, Hypertension, Vascular Disease, and Prevention p.223A.

Boekstegers et al. (1998). "Selective suction and pressure–regulated retroinfusion: An effective and safe approach to retrograde protection against myocardial Ischemia in patients undergoing normal and high risk percutaneous transluminal coronary angioplasty" *JACC*, vol. 31(7): 1525–1533.

Boekstegers et al. (2000). "Myocardial gene transfer by selective pressure–regulated retroinfusion of coronary veins" *Gene Therapy*, vol. 7:232–240.

Gerber et al. (2000). "The coronary venous system: An alternate portal to the myocardium for diagnostic and therapeutic procedures in invasive cardiology" *Current Interventional Cardiology Reports*, vol. 2: 27–37.

Von der Leyen et al. (1999). "A pressure–mediated nonviral method for efficient arterial gene and oligonucleotide transfer" *Human Gene Therapy*, vol. 10: 2355–2364.

* cited by examiner

*Primary Examiner*—Robert A. Schwartzman
*Assistant Examiner*—Katherine F Davis
(74) *Attorney, Agent, or Firm*—Bret E. Field; Bozicevic, Field & Francis

(57) ABSTRACT

Methods are provided for locally administering an agent to a host. Specifically, the subject methods provide for the local administration of an agent to an interstitial space of a host. In the subject methods, an agent is retroinfused into a vessel of a host, typically a vein, under conditions sufficient for the agent to enter an interstitial space of the host proximal to the vessel location into which the agent is retroinfused. In practicing the subject methods, the agent is administered to the host in combination with the production of vascular stress at the site of administration, where the vascular tissue stress is sufficient to provide for transport of the agent from the vascular site of deposition into the target interstitial space. In a preferred embodiment, the agent is retroinfused at a pressure sufficient to provide for mechanical stress on the vessel proximal to the target interstitial space. Also provided are kits for use in practicing the subject methods. The subject invention finds use in the local administration of a variety of different agents for treatment of a variety of different disease or other conditions.

19 Claims, 2 Drawing Sheets

Transvenous Pressure-Assisted Retrograde Infusion of Agents

Arrows indicate disruption of vascular wall, and exsudation of blood vessels into interstitium

METHODS AND KITS FOR LOCALLY ADMINISTERING AN ACTIVE AGENT TO AN INTERSTITIAL SPACE OF A HOST

FIELD OF THE INVENTION

The field of this invention is drug delivery, particularly localized drug delivery.

BACKGROUND OF THE INVENTION

One of the most complex and difficult problems that has plagued the medical profession and pharmaceutical industry for decades is the problem of achieving a therapeutic concentration of a drug locally at a target site within the body without producing unwanted systemic side effects. Parenteral or oral therapy of substances directed at treating disease in a particular internal organ or at a particular internal site must often be given in amounts dependent upon achieving critical systemic blood levels that can produce devastating side effects at other areas in the body. In yet other embodiments, the pharmacological agent being delivered may be expensive, making systemic administration costly. As such, systemic routes of administration are not always desirable or acceptable.

A number of protocols and delivery vehicles have been developed for use in local or regional administration of an active agent, where the agent is administered in such a way that it is confined to a particular area or location of the body, e.g. at or proximal to the target tissue. Such protocols include those in which the agent is delivered to the patient in a vehicle that acts as a depot for the agent, where a variety of synthetic and natural polymeric compositions have been used as depots in the local administration of active agents.

While a number of different protocols and vehicles have been developed for use in the local delivery of active agents, there continues to be a need for the development of new protocols of local agent delivery. Of particular interest would be the development of local delivery protocol which could provide for local delivery of an active agent into an interstitial space of a patient, preferably using a catheter based delivery system.

RELEVANT LITERATURE

U.S. Patents of interest include: U.S. Pat. Nos. 4,459,977; 4,689,041; 4,934,996; 5,011,468; 5,533,957; 5,597,377; 5,824,071; 5,885,238; 5,913,842 and 5,922,687. Also of interest are: Mann et al., Proc. Nat'l Acad. Sci. USA (May 1999) 96:6411–6; von der Leyen et al., Hum. Gene Ther. (September 1999) 10:2355–64; Baumbach et al., Catheter Cardiovasc. Interv. (May 1999) 47:102–106.

SUMMARY OF THE INVENTION

Methods are provided for locally administering an agent to a host. Specifically, the subject methods provide for the local administration of an agent to an interstitial space of a host. In the subject methods, an agent is retroinfused into a vessel of a host, typically a vein, under conditions sufficient for the agent to enter an interstitial space of the host proximal to the vessel location into which the agent is retroinfused. In practicing the subject methods, the agent is administered to the host in combination with the production of vascular stress at the site of administration, where the vascular tissue stress is sufficient to provide for transport of the agent from the vascular site of deposition into the target interstitial space. In a preferred embodiment, the agent is retroinfused at a pressure sufficient to provide for mechanical stress on the vessel proximal to the target interstitial space. Also provided are kits for use in practicing the subject methods. The subject invention finds use in the local administration of a variety of different agents for treatment of a variety of different disease or other conditions.

DESCRIPTION OF THE SPECIFIC EMBODIMENTS

Figure 1:
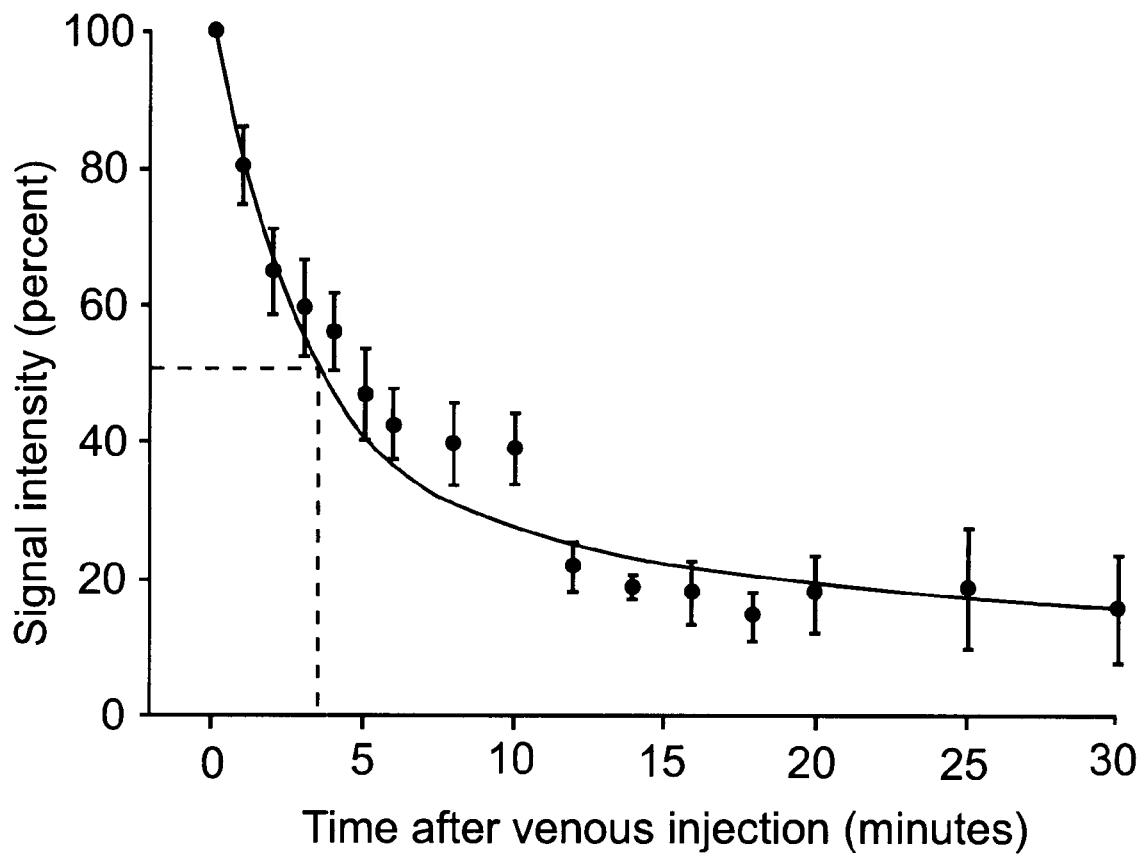
FIG. 1 provides a graphical result of the results observed in the study described in Example 1A, infra.

Methods are provided for locally administering an agent to a host. Specifically, the subject methods provide for the local administration of an agent to an interstitial space of a host. In the subject methods, an agent is retroinfused into a vessel of a host, typically a vein, under conditions sufficient for the agent to enter an interstitial space of the host proximal to the vessel location into which the agent is retroinfused. In many embodiments, the agent is administered to the host in combination with the production of vascular stress at the site of administration, where the vascular tissue stress is sufficient to provide for transport of the agent from the vascular site of deposition into the target interstitial space. In a preferred embodiment, the agent is retroinfused at a pressure sufficient to provide for mechanical stress on the vessel proximal to the target interstitial space. Also provided are kits for use in practicing the subject methods. The subject invention finds use in the local administration of a variety of different agents for treatment of a variety of different disease or other conditions.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

As summarized above, the subject invention provides methods of locally administering an active agent to a host. Specifically the subject invention provides methods for local administration of an active agent to an interstitial location of a host. By local administration is meant non-systemic, such that the active agent administered by the subject methods does not come into contact with more than a limited portion of the host. Generally, less than 50%, usually less than 25% and in many embodiments less than 10% by volume of the host will be contacted with an active agent that is delivered to the host by the methods of the subject invention. In many embodiments, the percent by volume of the host that comes into contact with the active agent following administration by the subject methods is much less than 10%. As such, the subject invention provides a method of regional delivery of an active agent to a host, where the regional delivery does not result in contact with more than a limited portion of the host's tissues with the active agent—i.e. the majority of the host is not contacted with an active agent when the agent is administered by the subject methods.

In the subject methods, the active agent is retroinfused into a vessel or vascular location of the host in a manner such that the agent enters into an interstitial space of the host. By retroinfused is meant that a physiologically acceptable flowable formulation of the active agent is introduced into the circulatory or vascular system of the host in a retrograde manner, i.e. in a manner that is against the normal blood flow direction in the vascular or circulatory location (i.e. vascular deposition site) in which the agent formulation is administered. Thus, the flowable agent formulation is administered via a retrograde infusion technique.

While the flowable agent formulation may, in principle, be administered to either an artery or vein, in many embodiments of the invention, the flowable formulation of the active agent is administered in a retrograde fashion to a venous location, i.e. to a venous deposition site. In these embodiments of the subject invention, a fluid delivery means is introduced into the circulatory system of the patient and advanced to the venous location proximal to the interstitial target site, i.e. the interstitial space into which agent delivery is desired. In other words, the distal end of the fluid delivery means through which fluid exits the delivery means is advanced to a vascular deposition site, e.g. venous deposition site, that is next to, adjacent or near the target interstitial site.

While any convenient fluid delivery means capable of accessing the vascular deposition site may be employed, generally the fluid delivery means is a catheter delivery means which is introduced into the host's circulatory system at a site remote from the vascular deposition site. A variety of different catheter delivery means are known to those of skill in the art and have been used in retroinfusion procedures, where such means include those described in U.S. Pat. Nos. 4,689,041; 5,533,957 and 5,913,842; the disclosure of which is herein incorporated by reference.

In preferred embodiments, the catheter fluid delivery system that is employed includes at least the following elements: (a) at least one distal port through which fluid leaves the catheter and enters the vascular deposition site; (b) a proximal attachment means for attaching the proximal end of the catheter to a fluid reservoir of the agent and other external components, e.g. a balloon inflation means; and (c) an occlusion means located next to the distal end of the catheter, where the occlusion means is capable of substantially occluding the vessel downstream of the target vascular site. In a preferred embodiment, the occlusion means is an inflatable balloon which can be inflated to substantially, if not completely, occlude the vessel at a proximal downstream location from the vascular deposition site.

In certain preferred embodiments, the fluid delivery means also includes a pressure sensing device that is capable of detecting the pressure at the vascular deposition site and relaying this information to the health care practitioner performing the process, e.g. through a data processing and display means. Pressure sensing devices that are suitable for use in the catheter systems are known in the art and include those described in U.S. Pat. Nos. 4,689,041; 4,934,996 and 5,533,957; the disclosures of which are herein incorporated by reference.

As summarized above, the flowable formulation of the agent is introduced into the vascular deposition site, e.g. venous deposition site, in a manner such that the agent enters into the interstitial space of the host near to, adjacent to or next to, i.e. in the vicinity of, the vascular site. By interstitial space is meant the region or tissue beyond the wall of the vascular site, e.g. beyond the intimal surface of the wall. In other words, the subject methods result in deposition of the agent in a space of the host that is on the non-blood side of the vessel into which the composition is administered. In yet another way of describing the subject method, the subject methods result in localizing the agent to a non-vascular space near to the vascular site of deposition. As such, the subject methods provide for delivery of the active agent to a tissue site beyond the blood vessel wall and the cells that make up the blood vessel wall, e.g. the intima and the endothelium of the blood vessel wall. Generally, the agent penetrates to a location that is at least beyond the outer cell layer of the vascular cell wall. As such, use of the subject methods results in introduction of the agent to a location that is next to, adjacent or near, but beneath the inner vessel wall. See e.g. FIG. 1 for a representative myocardial interstitial space into which agent may be introduced using the subject methods. As can be seen from FIG. 1, in entering the interstitial space, the agent travels beyond the vascular wall and cells associated therewith into the cells and tissues lying beyond the vascular wall. As such, an important feature of the subject methods is that they provide a means for readily administering an agent to interstitial locations and cells next to or associated therewith. Thus, for agents that act intracellularly or inside the cell, e.g. of non-vascular tissue or non-blood vessel tissue, the subject methods provide for deposition of the agent into the interstitial space next to the target cells, such that the agent may readily enter the target cells. Of certain embodiments of the particular interest, the interstitial space is interstitial space of the myocardial tissue, including epicardial and endocardial tissue.

A feature of the subject methods in many embodiments of the subject invention is that the agent is administered in combination with the application of stress to the vascular tissue associated with, i.e. at and near or next to, the vascular site of administration. More specifically, the subject methods are characterized by including the production of the stress on the vessels walls near to or at the vascular site of administration. The vascular wall stress that is produced in practicing the subject methods is sufficient to provide for the desired transport of the vascular administered agent to the target interstitial space. In other words, the amount of stress that is produced in the vasculature during practice of the subject methods is sufficient to provide for transport of the desired amount of agent from the vascular site of administration into the target interstitial space, where it is then available for uptake by the target cells in those embodiments where the agent is to act intracellularly. The stress that is produced on the vessel walls as part of the subject methods may be produced before or during administration of the active agent. As such, the stress will be placed on the vessel walls prior to administration in certain embodiments. In other embodiments, the stress will be placed on the vessel walls during administration.

The above described vascular wall stress may be produced in a number of different ways, where such ways include physical stress, chemical stress, combinations thereof, and the like. In many embodiments, the production of stress produces inflammation at the vascular site of deposition and proximal thereto, where the inflammation is desired and provides for enhanced activity of the active agent upon reaching the target interstitial space. For example, in methods where the active agent is an angiogenic inducing agent, the subject methods may be performed in a manner that produces inflammation at the vascular site, thereby enhancing the action of the angiogenic agent. As mentioned above, stress may be produced in the vessel wall using a single means or using a combination of means, e.g. a physical means and a chemical means. Physical means of producing stress in the vasculature include pressure means, application of external energy, etc, where chemical means of producing stress in the vasculature include chemical inflammatory agents, etc. Representative physical and chemical means of producing stress in the vasculature that may be employed in the subject methods are now described in greater detail below.

In one preferred embodiment of the subject methods, the flowable formulation of the active agent is introduced into a vascular deposition space in a manner such that mechanical stress is placed on the vessel at the site of deposition, where the mechanical stress is of sufficient magnitude to provide for passage of the active agent from the vascular space into the target interstitial space. In certain embodiments, the pressure is sufficient to result in distention of the vessel, whereby distention of the vessel is meant expansion of the vessel such that the cell wall in the region of fluid administration is stretched. Where distention is employed in the subject methods, the volume of the vascular deposition site bounded by the vessel walls typically increases in many embodiments by a factor of at least about 100%. Distention of the vessel walls results in increased permeability of the vessel walls to the active agent, where the permeability increases by a factor of at least about 5 and usually by a factor of at least about 10%.

In another preferred embodiment of the subject methods, the flowable formulation of the active agent is introduced into the vascular deposition space in a manner such that the mechanical stress is of sufficient magnitude to provide for actual disruption of the vessel wall. By disruption of the vessel wall is meant that the integrity of the wall is compromised such that actual passageways appear between the interior of the vessel and regions beyond the inner wall surface, i.e. between the vascular deposition site and the target interstitial space.

In those methods of the subject invention where the wall is subjected to mechanical stress to provide for the desired entry of the delivered active agent to the target interstitial space, a preferred means of providing the desired mechanical stress is to produce a high pressure environment in the target vascular site that is sufficient to provide the desired mechanical stress. The pressure of the high pressure environment that is produced in these embodiments may vary depending on the nature of the vascular deposition site, i.e. whether it is a vascular site of small volume, large volume, the blood pressure at the vascular deposition site, and the like. While exact pressures vary depending on the nature of the vascular deposition site, in many embodiments the pressure of the vascular deposition site is elevated to a value of at least about 50 mm Hg, usually at least about 60 mm Hg, where in certain embodiments the pressure may be elevated to a value that is at least about 1000 mm Hg or higher.

The elevated pressure at the vascular site may be produced using any convenient protocol. Generally, the elevated pressure will result from a combination of blockage or occlusion of the vascular site at a location downstream of the vascular site and introduction of the fluid at elevated pressure into the vascular deposition site. In these embodiments, power injectors may be employed to introduce the fluid at the desired elevated pressure. Alternatively, syringes or other fluid delivery means may be employed.

In yet other embodiments, retroinfusion of the agent to the target vascular site is accompanied by the application of energy to the vascular site under conditions sufficient to cause the desired stress in the vessel walls and thereby provide for migration of the active agent from the vascular site to the target interstitial location. In these embodiments, external energy is applied to the target vascular site to promote entry of the agent into the target interstitial space. Any means of applying external energy to the vascular site may be employed. As such, jets or other such means on a catheter device which are capable of providing varying external forces to the target vascular deposition site may be employed. Of particular interest in many embodiments is the use of ultrasound. The ultrasound can be applied during part of, or the entire time of, agent administration. There are several devices for the application of ultrasound to cardiovascular tissue known to those of skill in the art. For example, U.S. Pat. No. 4,808,153, the disclosure of which is herein incorporated by reference, describes an ultrasound apparatus to be used in an artery without damaging the artery, and U.S. Pat. No. 5,432,663, the disclosure of which is herein incorporated by reference, describes an apparatus for generating ultrasonic energy useful for removal of intravascular blockages. The ultrasound can be low frequency ultrasound. Another means that may be employed to apply external energy to target vascular site is to use a mechanical means of applying external energy. Mechanical means of interest include moving structures, e.g. rotating wires, which physically contact the target lesion and thereby apply physical external energy to the target lesion. Yet other means include localized application of heat, e.g. through a localized elevated temperature means.

One may also employ electroporation, where electrical energy is focused at the vascular deposition site such that the requisite stress is applied to the vessel walls and consequent transport of the agent to the interstitial target location is achieved. Catheter devices comprising electroporation means are known in the art and may be readily adapted for use in the subject methods. See e.g. U.S. Pat. No. 5,944,710, the disclosure of which is herein incorporated by reference.

It yet other embodiments, RF energy may be employed to provide the requisite vascular wall stress. A variety of catheter designs capable of directing RF energy to a vascular site are known and may be adapted for use in the subject methods. See e.g. U.S. Pat. Nos. 5,997,532; 5,954,719; 5,951,471; 5,944,716; 5,938,632; 5,938,599; 5,935,123; 5,931,835; 5,924,987; and the like.

Alternatively, or in addition to one or more of the above physical means, a variety of different chemical stress means may be employed to provide the requisite vascular tissue stress. Chemical means that may be employed include inflammatory agents, tissue disrupting agents, and the like, where such agents include small organic and inorganic compounds, e.g. acids, organic solvents, detergents and the like, as well as biological agents, e.g. enzymes (such as lipases, proteases, etc. ) and the like.

A feature of the subject invention is that deposition of the fluid composition of the agent to a single vascular site can be used to administer agent to a relatively large region of interstitial space. For example, in those preferred embodiments in which the fluid agent composition is retroinfused into a veinous site, the fluid agent composition can enter the entire upstream region of the vein (i.e. the portion of the vein moving from the site of administration against the direction of fluid flow). Thus, the agent may enter all of the veinous branches of the vein upstream of the site of administration. As such, active agent will enter the interstitial spaces associated with not only the vein at the site of administration but also with the veinous branches upstream of from the vascular site of deposition.

The interstitial tissue or region to which agent is administered during the subject method may be controlled or tailored in a number of different ways. For example, by proper selection of the vascular deposition site, one can limit the interstitial space to which agent is administered. Furthermore, one or more upstream branches can be occluded, e.g. through use of an embolization means, to further define or limit the interstitial space to which agent is administered.

The subject methods are suitable for use in delivery of agents to the interstitial spaces of a variety of different organs and tissues. Representative organs and tissues include: cardiac tissue, e.g. via coronary vein delivery; peripheral tissue, e.g. via peripheral veins; central nervous tissue such as the brain, e.g. via the great cerebral vein or branches thereof; hepatic tissue, e.g. via the hepatic vein or a branch thereof; kidneys, e.g. via a renal vein; and the like. Of particular interest in certain embodiments is the use of the subject methods for the delivery of agents to myocardial tissue, e.g. the epicaridum, endocardium, etc., of the myocardium.

The subject methods have a drug delivery efficiency to the target interstitial location such that an effective amount of the active agent readily enters the target interstitial space from the initial vascular site of deposition. In the subject methods, the efficiency is generally such that at least about 1% by weight of the agent initially deposited in the vascular site reaches the target interstitial space, wherein in many embodiments the efficiency is at least about 10% and in certain embodiments is at least about 20%. As compared to a control situation in which an analogous method is employed but vascular wall stress or damage is not provided, as is requisite in the subject methods, the efficiency of administration of the agent increases by at least about 10 fold, and in many embodiments by as much as 25 or even 50 fold.

The above described methods may be used to introduce a wide variety of active agents to a target interstitial space. Active agents of interest include both small molecule active agents, as well as macromolecular or large molecule active agents (e.g. molecules having a molecular weight in excess of 5000 daltons, usually 10,000 daltons), including biological agents, where the administration of biological agents and derivatives thereof is of particular interest in many embodiments. Representative biological agents of interest include, but are not limited to, e.g. nucleic acids, such as oligonucleotides and polynucleotides, both ribo and deoxyribo, as well as mimetic thereof, e.g. PNAs; polypeptides and proteins; polysaccharides; lipids; and mimetics thereof.

Of particular interest in many embodiments is the use of the subject methods to deliver therapeutic nucleic acids. The subject methods may be used to deliver a wide variety of therapeutic nucleic acids. Therapeutic nucleic acids of interest include genes that replace defective genes in the target host cell, such as those responsible for genetic defect based diseased conditions; genes which have therapeutic utility in the treatment of cancer; and the like. Specific therapeutic genes for use in the treatment of genetic defect based disease conditions include genes encoding the following products: factor VIII, factor IX, β-globin, low-density protein receptor, adenosine deaminase, purine nucleoside phosphorylase, sphingomyelinase, glucocerebrosidase, cystic fibrosis transmembrane regulator, α-antitrypsin, CD-18, ornithine transcarbamylase, arginosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, and the like. Cancer therapeutic genes that may be delivered via the subject methods include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like. The subject methods can be used to not only introduce a therapeutic gene of interest, but also any expression regulatory elements, such as promoters, and the like, which may be desired so as to obtain the desired temporal and spatial expression of the therapeutic gene.

The subject methods may also be employed to deliver a variety of peptide and protein therapeutic agents. Representative peptide and protein therapeutic agents of interest include: potent cytokines, including various hematopoietic factors such as G-CSF, GM-CSF, M-CSF, MGDF, the interferons (alpha, beta, and gamma), interferon consensus, the interleukins (1–12), erythropoietin (EPO), fibroblast growth factor, TNF, TNFbp, IL-1ra, stem cell factor, nerve growth factor, GDNF, BDNF, NT3, platelet-derived growth factor, and tumor growth factor (alpha, beta), osteoprotegerin (OPG), and the like.

In yet other embodiments, the agent administered to the interstitial space via the subject methods is an imaging agent or dye. Imaging agents of particular interest include: non-ionic imaging agents, e.g. CONRAY™, OXILAN™, and the like.

In yet other embodiments, the agent that is administered to the interstitial space is not an active agent in its own right, but provides for the presence of an active agent in the target interstitial site. As such, a cell which provides for the presence of a desired compound in the interstitial target site, e.g. the presence of a desired protein which is expressed and secreted by the cell into the target interstitial space, may be administered via the subject methods. Alternatively, an agent that recruits a subsequently systemically administered agent to the interstitial target site may be employed. For example, an agent exhibiting a specific epitope may be administered to the interstitial site. Subsequent to administration an antibody, potentially conjugated to an active agent, may be systemically administered upon which the antibody homes to and is recruited to the target interstitial site.

In the subject methods, the agent may be administered in any convenient fluid vehicle. In many embodiments, the agent is dissolved in a fluid delivery vehicle. The fluid delivery vehicle may be any convenient fluid which is suitable for vascular introduction, particularly intravenous administration. In these embodiments, the vehicle is generally an aqueous fluid, where the aqueous fluid may or may not include a number of additional optional components, e.g. electrolytes (such as $Cl^-$, $K^+$, $Na^+$, $Ca^{2+}$ etc.), nutrients (e.g. amino acids), oncotic agents (e.g. dextran), pH modulating agents (e.g. lactate), etc. Generally, the aqueous fluid is made up of water for injection to which one of more optional agents such as the representative ones described above have been added.

Depending on the nature of the active agent, the active agent may be administered in combination with a vector or delivery means that provides a one or more desired functions, e.g. as a depot of the agent, to enhance delivery of the agent into a target cell, etc. Thus, in an alternative embodiment of the above described methods, the agent is administered in combination with a depot means, where the depot means and agent are administered under pressure sufficient to lodge the depot means/agent at the vascular site of administration or deposition such that agent enters the target interstitial space proximal to the vascular site of administration where the depot means has been lodged. Any convenient depot means may be employed, so long as the depot is compatible with intravascular, e.g. intravenous, administration. Depot means of interest include particulate or viscous compositions that, when administered under pressure, lodge in the vascular space to which they are administered such that the active agent is capable of entering the target interstitial space from the vascular site of administration. Specific depot materials of interest include microcoils, e.g. platinum or stainless steel microcoils, polyvinyl alcohol sponges, bioglues (e.g. cyanoacrylate glues), precipitative materials, and the like, where representative materials are disclosed in U.S. Pat. No. 5,925,683, the disclosure of which is herein incorporated by reference.

Where the active agent is a nucleic acid e.g. DNA or RNA encoding a therapeutic produce, antisense, etc., a variety of different nucleic acid vectors may be employed. Alternatively, an agent that modulates the distribution of the vector in the multicellular organism may be employed. For example, lipid based, e.g. liposome, vehicles may be employed. Patents disclosing such methods include: U.S. Pat. Nos. 5,877,302; 5,840,710; 5,830,430; and 5,827,703, the disclosures of which are herein incorporated by reference. Alternatively, polylysine based peptides may be employed as carriers, and the like. (Brooks, A. I., et al. 1998, J. Neurosci. Methods V. 80 p: 137–47; Muramatsu, T., Nakamura, A., and H. M. Park 1998, Int. J. Mol. Med. V. 1 p: 55–62). In yet other embodiments, the system components may be incorporated onto viral vectors, such as adenovirus derived vectors, sindbis virus derived vectors, retroviral derived vectors, etc. hybrid vectors, and the like. The above vectors and delivery vehicles are merely representative. Any vector/delivery vehicle combination may be employed, so long as it provides for desired delivery of the active agent from the interstitial site of administration.

As discussed above, the above described methods of the subject invention result in the localized administration of an active agent into a target interstitial space of a host, where the agent is administered via the vascular system of the host. In other words, the subject methods provide a means for delivering an agent to a target interstitial space from a vascular site of administration, where the target interstitial space is not within a vessel e.g. is not within a vein.

The subject methods may be used in the delivery of active agents to a variety of hosts. Generally such hosts are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts will be humans.

The subject methods find use in a number of different applications. Of particular interest is the use of the subject methods to locally administer one or more active agents to a host, where administration of the active agent(s) is desired to treat a disease or other condition of the host. Representative disease conditions in which the subject invention finds use include: cardiovascular disease conditions, treatment of cellular proliferative diseases, gene therapy applications, central nervous system disorders, renal disease conditions, peripheral vascular disease conditions, and the like.

By way of further illustration, the following illustrative and representative cardiovascular and antineoplastic disease conditions are described. One representative type of cardiovascular disease condition in which the subject methods find use are those in which it is desired to deliver angiogenic agents to the myocardium, e.g. the interstitial space of myocardial tissue, including the epicardium, endocardium etc. In this embodiment of the subject methods, a fluid composition of the angiogenic agent is retroinfused into a coronary vessel, typically a coronary vein, in conjunction with the application of stress to the coronary vessel walls, e.g. by administering the fluid agent at high pressure, e.g. in excess of 50 mm Hg. Angiogenic factors of interest include those described in U.S. Pat. Nos.: 5,972,903; 5,941,868; 5,866,561; 5,798,386; 5,756,453; 5,470,831; 5,356,874; 5,332,804; 5,318,957; 5,238,925; 5,171,845; 5,137,734; 4,921,838; 4,916,073; 4,900,673; 4,897,464; 4,895,838; 4,888,324; 4,879,312; 4,727,137; 4,721,672; 4,710,490; 4,699,788; 4,698,301; 4,529,590; 4,503,038; 4,273,871 and the like, the disclosures of which are herein incorporated by reference. In certain preferred embodiments, the angiogenic factor is administered in a manner that produces inflammation at the site of administration, as described above.

Another specific representative application in which the subject methods find use in the treatment of hepatic cellular proliferative diseases, e.g. liver cancer. In such applications, an antineoplastic agent is retroinfused into the hepatic vein in conjunction with application of stress to the walls of hepatic vein. In many embodiments, the antineoplastic agent is retroinfused into the hepatic vein under pressure such that there is structural disruption of the veinous walls and transport of the active agent to the hepatic interstitial space and cells located therein. Representative antineoplastic agents which may be employed in this representative method include those described above.

Also provided by the subject invention are kits for use in practicing the subject methods. The kits of the subject invention include at least one of: (i) a catheter, and (ii) the active agent, where in certain embodiments the kits will include a catheter (or analogous intravenous fluid delivery means) and an active agent. The active agent may be present as a fluid composition or as a storage stable dried composition that is reconstituted prior to administration, e.g. a lyophilized preparation, etc. In addition, the kit may include a fluid delivery vehicle, such as water for injection or intravenous fluid, which may be modified to include one or more additional optional components such as those described above, e.g. electrolytes, nutrients, oncotic agents, etc.

In addition to at least one of (a) the fluid delivery means and (b) the active agent(s), the subject kits also include instructions for administering the active agent according to the subject invention. Specifically, the subject kits also include instructions for using the components of the kit in methods of retroinfusing an agent in a manner that results in localized delivery of the agent to an interstitial space. The instructions for practicing the above described methods or variations thereof, e.g. variations which include the administration of a pH elevating fluid as described in U.S. patent application Ser. No. 09/425,826, now U.S. Pat. No. 6,290, 689 the disclosure of which is herein incorporated by reference, etc., are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging)

etc. In other embodiments, the instructions are present as an electronic storage data file present on a suitable computer readable storage medium, e.g. CD-ROM, diskette, etc.

The following examples are offered by way of illustration and not by way of limitation.

EXPERIMENTAL

EXAMPLE 1

A.

Background: Therapeutic angiogenesis is a promising option for patients with refractory angina unsuitable for revascularization, but current delivery methods either require open-chest surgery or provide only short-lived, transient exposure to growth factors. This study assessed the feasibility of percutaneous coronary venous cannulation and selective regional injection as a novel approach to local myocardial drug delivery.

Methods and Results: In 13 anesthetized pigs the coronary sinus was cannulated percutaneously and a balloon-tipped catheter was advanced to the anterior interventricular vein (AIV) or middle cardiac vein (MCV). During balloon occlusion, selective venous injection of radiographic contrast (diatrizoate) caused localized myocardial staining. Injection was performed with hyperbaric pressure in 8/13 cases (61%). In the total group, videodensitometric analysis showed that diatrizoate persisted for at least 30 minutes, with 50% clearance over approximately the first 4 minutes (FIG. 1). Venous injection of Evans Blue dye showed that localized, regional infiltration was reproducibly accomplished in targeted myocardial regions: the left ventricular apex, anterior interventricular septum and anterior wall via the AIV and the inferoposterior wall via the MCV.

Conclusions: The percutaneous coronary venous route is a favorable delivery approach for therapeutic angiogenic substances, being reproducibly accessible and facilitating selective regional myocardial delivery and persistence of delivered substances.

B. Intracardiac Venous System as a Novel Conduit for Local Drug Delivery

Background: Effective strategies for administering angiogenic factors involve either multiple myocardial injections or intracoronary delivery into highly diseased conduits. Alternatively, access to cardiac venous system through the coronary sinus provides an extensive network of vessels for regional delivery of angiogenic agents to the distal myocardium.

Methods: Five swine underwent simultaneous right and left heart cardiac catheterization. A 7F balloon tip catheter over a guidewire was used to cannulate the anterior interventricular vein (AIV). 15 $\mu$m fluorescent microspheres were used to determine the territory of myocardium that drains into the AIV, and would be potentially available for drug delivery. A different color set of microspheres was used to label the left anterior descending artery territory (through subselective engagement of LAD). All injections were performed over constant time and pressure. Simultaneous ventricular end diastolic pressure (LVEDP), coronary wedge pressure, and distal venous wedge pressure were measured during the balloon inflation. The hearts were harvested and a circumferential sample was divided into eight segments; each segment was divided further into the epicardial and endocardial layers. These samples were processed for microspheres sedimentation, and subjected to scanning fluorometery to determine the amount of different color microspheres in each region. Results: There was no significant increase in the LVEDP, and only transient elevation of VWP during the injections (range of 5 to 30 mm Hg). The concentration of microspheres in the LAD territory was similar in both LAD and AIV injections (93%±3.5 vs. 81%±7.0, respectively). 68% of the microspheres delivered through the AIV localized to the epicardial layer of myocardium vs. 53% delivered through the LAD (endocardial localization after AIV and LAD injections were 32% and 47%, respectively).

Conclusion: These data demonstrate the feasibility of using the cardiac venous system for regional myocardial reagent delivery.

EXAMPLE 2

Figure 2:
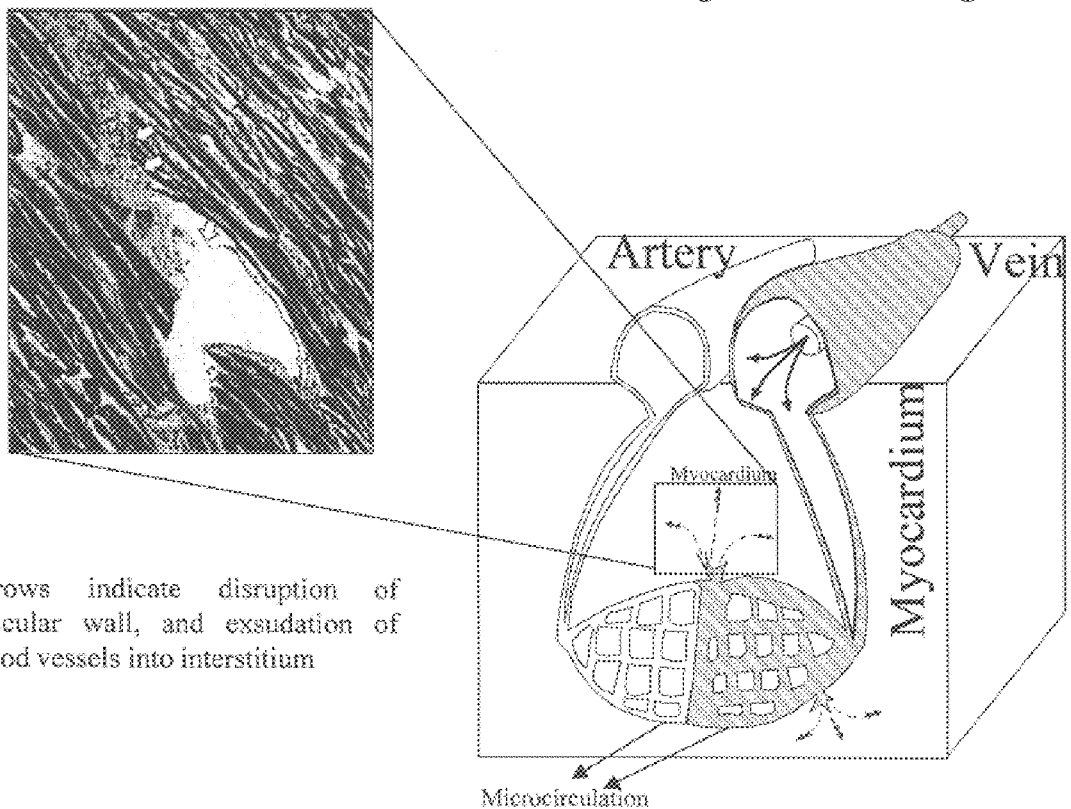
FIG. 2 provides a representation of transvenous pressure-assisted delivery according to the subject invention and a computer generated micrograph of an actual myocardium from which the representation of FIG. 2 was derived.

FIG. 2 provides a representation of administration according to the subject methods in which the vessel walls are disrupted by pressure applied during retrograde administration of the agent, thereby providing for entry of the agent into the interstitial space.

It is evident from the above discussion that the subject invention provides an important new means for locally administering an active agent to a host. Specifically, the subject invention provides a method for locally administering an active agent to an interstitial target site proximal to a vessel. The subject methods are suitable for use in the delivery of a wide variety of different agents, and are particularly suited for use in the delivery of biological agents, such as polypeptides and nucleic acids. One advantage of the subject methods is that they provide a new and convenient methodology for delivering active agents, including biological agents, to the myocardium. Other advantages of the subject methods include the ability to deliver agent to a large region of interstitial space from a single administration point. Additional advantages include the ability of the host to tolerate the mode of administration such that damage caused by the route of administration, if any, is outweighed by the benefits provided by the subject method of administration and the ability to produce inflammation at the site of administration, when desired. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of locally administrating an active agent to a host, said method comprising:

retroinfusing said agent into a vascular vessel of said host under conditions sufficient to produce a disruption in said vessel and for said agent to enter an interstitial space of said host through said disruption so that said agent is locally administered to said host.

2. The method according to claim 1, wherein said vessel is a vein.

3. The method according to claim 1, wherein said retroinfusing comprises providing stress to said vascular vessel at a site at least proximal to said interstitial space.

4. The method according to claim 1, wherein said method further comprises using depot means.

5. The method according to claim 1, wherein said method further comprises administration of energy to said vessel.

6. The method according to claim 1, wherein said interstitial space is myocardial interstitial space.

7. The method according to claim 3, wherein said retroinfusing comprises administering said agent at a pressure sufficient to produce at least a mechanical stress on said vessel.

8. A method of locally administering an active agent to a host, said method comprising:

retroinfusing said agent into a vein of said host under conditions sufficient to produce a disruption in said vessel and for said agent to enter an interstitial space of said host through said disruption so that said agent is locally administered to said host.

9. The method according to claim 8, wherein said retroinfusing comprises administering said agent at a pressure sufficient to produce at least a mechanical stress on said vein.

10. The method according to claim 8, wherein said agent is a biological agent selected from the group consisting of peptides, proteins, nucleic acids, lipids, polysaccharides, and mimetics thereof.

11. The method according to claim 8, wherein said method further comprises producing inflamation in said vascular vessel.

12. The method according to claim 8, wherein said interstitial space is myocardial interstitial space.

13. The method according to claim 9, wherein said pressure is sufficient to at least distend said vein.

14. The method according to claim 9, wherein said pressure is sufficient to disrupt said vein.

15. A method of locally administering an active agent to a host, said method comprising:

retroinfusing said agent into a vein of said host with a catheter and at a pressure sufficient to produce a disruption on said vein such that said agent enters an interstitial space proximal to the vein through said disruption;

whereby said agent is locally administered to said host.

16. The method according to claim 15, wherein said pressure is sufficient to at least distend said vein.

17. The method according to claim 16, wherein said pressure is sufficient to disrupt said vein.

18. The method according to claim 16, wherein said agent is a biological agent selected from the group consisting of peptides, proteins, nucleic acids, lipids, polysaccharides, and mimetics thereof.

19. The method according to claim 16, wherein said method further comprises producing inflamation in said vascular vessel.

\* \* \* \* \*